US009056079B2

(12) United States Patent
Agam et al.

(10) Patent No.: US 9,056,079 B2
(45) Date of Patent: Jun. 16, 2015

(54) MOLECULES INTERFERING WITH BINDING OF CALBINDIN TO INOSITOL MONOPHOSPHATASE FOR THE TREATMENT OF MOOD DISORDERS

(75) Inventors: Galila Agam, Omer (IL); Orna Almog, Omer (IL); Itzchak Levi, Modi'in Illit (IL); Yael Eskira, Beer Sheva (IL); Yuly Bersudsky, Beer Sheva (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 248 days.

(21) Appl. No.: 12/991,700

(22) PCT Filed: May 14, 2009

(86) PCT No.: PCT/IL2009/000488
§ 371 (c)(1),
(2), (4) Date: Nov. 9, 2010

(87) PCT Pub. No.: WO2009/138987
PCT Pub. Date: Nov. 19, 2009

(65) Prior Publication Data
US 2011/0076347 A1 Mar. 31, 2011

Related U.S. Application Data

(60) Provisional application No. 61/071,744, filed on May 15, 2008, provisional application No. 61/193,665, filed on Dec. 15, 2008.

(51) Int. Cl.
*A61K 38/08* (2006.01)
*C07K 7/06* (2006.01)
*A61K 33/14* (2006.01)
*C07K 5/09* (2006.01)
*C07K 7/08* (2006.01)
*C07K 14/47* (2006.01)
*C12N 9/16* (2006.01)
*A61K 38/00* (2006.01)

(52) U.S. Cl.
CPC .............. *A61K 33/14* (2013.01); *A61K 38/08* (2013.01); *C07K 5/0815* (2013.01); *C07K 7/06* (2013.01); *C07K 7/08* (2013.01); *C07K 14/4713* (2013.01); *C12N 9/16* (2013.01); *A61K 38/00* (2013.01)

(58) Field of Classification Search
None
See application file for complete search history.

(56) References Cited

U.S. PATENT DOCUMENTS

2003/0170668 A1 9/2003 Detera-Wadleigh et al.
2004/0126377 A1 7/2004 Meissner
2007/0060550 A1* 3/2007 Mudge ........................ 514/102
2007/0099839 A1 5/2007 Stefanidakis et al.

FOREIGN PATENT DOCUMENTS

WO    WO 04/001008    * 12/2003

OTHER PUBLICATIONS

Elhadad et al. "Interaction of calbindin D28K and inositol monophosphatase in human postmortem cortex: possible implications for bipolar disorder", Bipolar Disorders 2005, pp. 42-48.*
Kim et al., A review of the possible relevance of inositol and the phosphatidylinositol second messenger system (PI-cycle) to psychiatric disorders-focus on magnetic resonance spectroscopy (MRS) studies, Hum Psychopharmacol Clin Exp 2005; pp. 309-326.*
Yung, "A review of clinical trials of lithium in medicine", Phamacol Biochem Behav, 1984, Abstract, print p. 1 of 2.*
Richman et al. "The Effect of Lithium Carbonate on Chemotherapy-Induced Neutropenia and Thrombocytopenia", American Journal of Hematology, 1984, pp. 313-323.*
Harwood, Lithium and bipolar mood disorder: the inositol-depletion hypothesis revisited, Molecular Psychiatry, 2005, pp. 117-126.*
Levi et al., "Inhibition of inositol monophosphatase (IMPase) at the calbindin-D28k binding site: Molecular and behavioral aspects", European Neuropsychopharmacology, 2013, pp. 1806-1815.*
Brown et al., "Lithium: the pharmachodynamic actions of the amazing ion", Therapeutic Advances in Psychopharmacology, 2013, 163-176.*
Atack, Inositol Monophosphatase Inhibitors—Lithium Mimetics?, Medicinal Research Reviews, Vo. 17, No. 2, 215-224 (1997).
Harwood et al., Commentary—Search for a common mechanism of mood stabilizers, Biochemical Pharmacology 66 (2003) 179-189.
Hallcher et al., The Effects of Lithium Ion and Other Agents on the Activity of myo-Inositol-1-phosphatase from Bovine Brain, The Journal of Biol.ogical Chemistry, vol. 255, No. 22, Issue of Nov. 25, pp. 10896-10901, 1980.
Ohnishi et al, Spatial Expression Patterns and Biochemical Properties Distinguish a Second myo-Inositol Monophosphatase IMPA2 from IMPA1, The Journal of Biological Chemistry vol. 282, No. 1, pp. 637-646, Jan. 5, 2007.
Fauroux et al., Review Article—Inhibitors of Inositol Monophosphatase, J. Enzyme Inhibition 1999 (12 pages).
ISR of the corresponding PCT application (4 pages) mailed Dec. 17, 2009.
Berggard et al, Myo-Inositol monophosphatase . . . calbindin D28k, J. Biol. Chem., Nov. 1, 2002, vol. 277, No. 44, pp. 41954-41959.
Written Opinion of the corresponding PCT application (6 pages) mailed Dec. 17, 2009.
Chapter 200: Mood disorders: In: Anonymous: "The Merck Manual of Diagnosis and Therapy", 2006, Merck research Laboratories, Whitehouse Station, NJ, xp0026341, ISBN: 0911910182, pp. 1703-1713.
Kojetin et al. "Structure, binding interface and hydrophobic transitions of Ca2+-loaded calbindin-D28K", Nature Structural & Molecular Biolofy, vol. 13, No. 7, Jun. 5, 2006, pp. 641-647, xp055061216, ISSN: 1545-9993.

(Continued)

*Primary Examiner* — Karlheinz R Skowronek
*Assistant Examiner* — Lianko Garyu
(74) *Attorney, Agent, or Firm* — Roach Brown McCarthy & Gruber, P.C.; Kevin D. McCarthy

(57) ABSTRACT

This invention provides derivatives of dodecapeptide ISSIKEKYPSHS (SEQ ID NO: 11) which interfere with binding of calbindin to inositol monophosphatase, and their use in treating mood disorders.

4 Claims, No Drawings

(56) References Cited

OTHER PUBLICATIONS

Communication from a foreign patent office in a counterpart foreign application—Supplementary European Search Report—7 pages, mailed May 13, 2013.
Berggard et al., "Myo-Inositol monophosphatase is an activated target of calbindin D28k", Journal of Biological Chemistry, American Society for Biochemistry and Molecular Biology, vol. 277, No. 44, Nov. 1, 2002.
Levi et al., "Inhibition of inositol monophosphatase (IMPase) at the calbindin-D28k binding site: Molecular and behavioral aspects" European Neuropsychopharmacology, , http://dx.doi.org/10.1016/j.euroneuro.2013.02.004.
Damri et al., "Molecular effects of lithium are partially mimicked by inositol-monophosphatase (IMPA)1 knockout mice in a brain region-dependent manner"—submitted on Feb. 16, 2014.
Toker et al., "Inositol-Related Gene Knockouts Mimic Lithium's Effect on Mitochondrial Function", Neuropsychopharmacology (2014) 39, 319-328.
Sarkar et al., "Lithium induces autophagy by inhibiting inositol monophosphatase"; The Journal of Cell Biology, vol. 170, No. 7, Sep. 26, 2005 1101-1111.
Feng et al., "Combined lithium and valproate treatment delays disease onset, reduces neurological deficits and prolongs survival in an amyotrophic lateral sclerosis mouse model"; Neuroscience. Aug. 26, 2008; 155(3):567-72.
Fornai et al., "Lithium delays progression of amyotrophic lateral sclerosis"; Proc Natl Acad Sci U S A. Feb. 12, 2008;105 (6):2052-7.
Liu et al., "Lithium reverses increased rates of cerebral protein synthesis in a mouse model of fragile X syndrome"; Neurobiology of Disease, vol. 45, Issue 3, Mar. 2012, pp. 1145-1152.
Shimohama et al., "Alteration of myo-inositol monophosphatase in Alzheimer's disease brains"; Neuroscience Letters, vol. 245, Issue 3, Apr. 10, 1998, pp. 159-162.

* cited by examiner

SEQUENCE LISTING

```
<160> NUMBER OF SEQ ID NOS: 11

<210> SEQ ID NO 1
<211> LENGTH: 6
<212> TYPE: PRT
<213> ORGANISM: Artificial
<220> FEATURE:
<223> OTHER INFORMATION: Peptide derived from the segment including
      residues 55-66 of IMPase

<400> SEQUENCE: 1

Ile Lys Glu Lys Tyr Pro
1               5

<210> SEQ ID NO 2
<211> LENGTH: 6
<212> TYPE: PRT
<213> ORGANISM: Artificial
<220> FEATURE:
<223> OTHER INFORMATION: Peptide derived from the segment including
      residues 55-66 of IMPase

<400> SEQUENCE: 2

Ile Lys Ala Lys Tyr Pro
1               5

<210> SEQ ID NO 3
<211> LENGTH: 6
<212> TYPE: PRT
<213> ORGANISM: Artificial
<220> FEATURE:
<223> OTHER INFORMATION: Peptide derived from the segment including
      residues 55-66 of IMPase

<400> SEQUENCE: 3
```

```
Ile Lys Glu Ala Tyr Pro
1               5

<210> SEQ ID NO 4
<211> LENGTH: 6
<212> TYPE: PRT
<213> ORGANISM: Artificial
<220> FEATURE:
<223> OTHER INFORMATION: Peptide derived from the segment including
      residues 55-66 of IMPase

<400> SEQUENCE: 4

Ile Ala Glu Lys Tyr Pro
1               5

<210> SEQ ID NO 5
<211> LENGTH: 6
<212> TYPE: PRT
<213> ORGANISM: Artificial
<220> FEATURE:
<223> OTHER INFORMATION: Peptides derived from the segment including
      residues 55-66 of IMPase

<400> SEQUENCE: 5

Ser Tyr Glu His Tyr Pro
1               5

<210> SEQ ID NO 6
<211> LENGTH: 6
<212> TYPE: PRT
<213> ORGANISM: Artificial
<220> FEATURE:
<223> OTHER INFORMATION: Peptide derived from the segment including
      residues 55-66 of IMPase

<400> SEQUENCE: 6

Ile Ala Glu Ala Tyr Pro
1               5

<210> SEQ ID NO 7
<211> LENGTH: 6
<212> TYPE: PRT
<213> ORGANISM: Artificial
<220> FEATURE:
<223> OTHER INFORMATION: Peptides derived from the segment including
      residues 55-66 of IMPase

<400> SEQUENCE: 7

Lys His Ile Lys Pro Ser
1               5

<210> SEQ ID NO 8
<211> LENGTH: 6
<212> TYPE: PRT
<213> ORGANISM: Artificial
<220> FEATURE:
<223> OTHER INFORMATION: Peptide derived from the segment including
      residues 55-66 of IMPase

<400> SEQUENCE: 8

Ile Ala Ala Ala Tyr Pro
1               5

<210> SEQ ID NO 9
<211> LENGTH: 5
<212> TYPE: PRT
<213> ORGANISM: Artificial
<220> FEATURE:
```

```
<223> OTHER INFORMATION: Peptide derived from the segment including
      residues 55-66 of IMPase

<400> SEQUENCE: 9

Ile Lys Glu Lys Tyr
1               5

<210> SEQ ID NO 10
<211> LENGTH: 3
<212> TYPE: PRT
<213> ORGANISM: Artificial
<220> FEATURE:
<223> OTHER INFORMATION: Peptide derived from the segment including
      residues 55-66 of IMPase

<400> SEQUENCE: 10

Lys Glu Lys
1

<210> SEQ ID NO 11
<211> LENGTH: 12
<212> TYPE: PRT
<213> ORGANISM: Artificial
<220> FEATURE:
<223> OTHER INFORMATION: Residues 55-66 of IMPase

<400> SEQUENCE: 11

Ile Ser Ser Ile Lys Glu Lys Tyr Pro Ser His Ser
1               5                   10
```

US 9,056,079 B2

MOLECULES INTERFERING WITH BINDING OF CALBINDIN TO INOSITOL MONOPHOSPHATASE FOR THE TREATMENT OF MOOD DISORDERS

REFERENCE TO CO-PENDING APPLICATIONS

This application claims priority as a nationalized U.S. patent application of PCT/IL2009/000488 filed on May 14, 2009; which claims priority to (a) U.S. provisional application Ser. No. 61/071,744 filed on May 15, 2008 and (b) U.S. provisional application Ser. No. 61/193,665 filed on Dec. 15, 2008.

FIELD OF THE INVENTION

The present invention relates to interfering with the activating effect that the protein calbindin has on inositol monophosphatase, thereby affecting signaling cascades affected by lithium therapy.

BACKGROUND OF THE INVENTION

Mood disturbances which may require clinical attention affect more than 10% of the adult population during their lifetime, and the occurrence of bipolar disorders (manic-depressive illness) is estimated as high as 5% in the general population (Merck Index, 1999). A main therapy for the mood disorders comprises delivering lithium salts (Li); however, Li has a narrow therapeutic window and exhibits toxic effects, requiring careful blood monitoring. Besides, Li at therapeutic levels exhibits adverse effects, including gross tremor, persistent headache, vomiting, mental confusion, and possibly cardiac arrhythmias and various chronic problems, and 30% of the patients do not respond to the treatment. At certain stages and for some cases, anticonvulsants and antipsychotics are also used in treating bipolar disorders, but they may be teratogenic, and 30% of the patients do not respond. Therefore, an urgent need is felt for new drugs.

The mechanism of the therapeutic effect of Li is still unknown despite numerous reported biochemical effects. Inositol monophosphatase (IMPase) remains a viable target [Harwood and Agam, 2003, Ohnishi et al., 2007]. IMPase has an important role in the phosphatidylinositol (PI) signaling system since it catalyzes the dephosphorylation of myo-inositol monophosphates to free myo-inositol. It was shown that therapeutically-relevant lithium concentrations (0.5-1.5 mM) exert an uncompetitive inhibition on IMPase with a Ki of 0.8 mM, probably by binding to the $Mg^{2+}$-binding sites of the enzyme [Hallcher and Sherman, 1980]. Reduced activity of IMPase may lead to depletion of intracellular free myo-inositol, which is used in the re-synthesis of the signalling precursor PI. Based on this, several pharmaceutical companies have tried to synthesize IMPase inhibitors targeting the substrate site of the enzyme, such as terpenoid and tropolone analogues [Fauroux and Freeman, 1999], and bisphosphonates, but their development to clinical mood stabilizers was limited for a variety of reasons. [Atack, 1997]. It is therefore an object of this invention to provide a new system for reducing the activity of IMPase.

It is another object of this invention to reduce IMPase without the use of Li.

It is still another object of this invention to positively affect mood disorders without the drawbacks of prior art methods.

Other objects and advantages of present invention will appear as description proceeds.

SUMMARY OF THE INVENTION

This invention relates to a method of reducing inositol monophosphatase (IMPase) activity, comprising i) providing a small molecule which interferes with binding of human calbindin D28k (calbindin) to human IMPase in vitro; and ii) contacting human IMPase in the presence of human calbindin with said small molecule, thereby reducing the activating effect of said calbindin on said IMPase. The term "small molecule" as used herein means a molecular structure of a molecular weight up to about 2000 Dalton, for example up to 1000 Dalton; the term stands in contrast to large molecules such as polypeptides. Said small molecule is, in a preferred embodiment, a peptide comprising from six to twelve amino acids, or its functional equivalent, or a pharmaceutically acceptable salt thereof, said peptide having sequence SEQ ID NO:11 (ISSIKEKYPSHS) or a contiguous fragment thereof, in which up to three amino acid residues are replaced. Examples of such peptides include a contiguous fragment comprising from six to eleven amino acids of sequence SEQ ID NO:11 in which up to three amino acid residues are replaced (by other amino acids), a contiguous fragment comprising from six to eleven amino acids of sequence SEQ ID NO:11 in which up to two amino acid residues are replaced, a contiguous fragment comprising from six to ten amino acids of sequence SEQ ID NO:11 in which up to two amino acid residues are replaced, or a contiguous fragment comprising from six to nine amino acids of sequence SEQ ID NO:11 in which up to two amino acid residues are replaced. Said functional equivalent comprises a peptide mentioned above derivatized by a reaction of terminal carboxyl or amino group, or by a reaction of side chains of said amino acid residues; said reaction may comprise, for example, alkylation or esterification or cyclization. The term "functional equivalent" as used herein means a peptide derivative which interferes with binding of human calbindin D28k to human IMPase in vitro. In a preferred embodiment of the invention, said small molecule causes at least 50% reduction of human IMPase activity in the presence of human calbindin D28k in vitro.

The invention relates to a method of treating mood disorders comprising reducing inositol monophosphatase (IMPase) activity, comprising i) providing a small molecule which interferes with binding of human calbindin D28k to human IMPase in vitro; and ii) contacting human IMPase in the presence of human calbindin D28k with said small molecule, thereby reducing the activating effect of said calbindin on said IMPase. In a preferred embodiment of the invention, a method of treating mood disorders is provided, comprising i) providing a peptide comprising from six to twelve amino acids, or its functional equivalent, or a pharmaceutically acceptable salt thereof, said peptide having sequence SEQ ID NO:11 or a contiguous fragment thereof, in which up to three amino acid residues are replaced; and ii) administering said peptide or equivalent or salt thereof to a subject in need of such treatment. In one aspect of the invention, said small molecule may substitute for Li in treating a mood disorder. In another aspect of the invention, said small molecule is used simultaneously with Li which may be administered in lower doses.

The invention provides a peptide comprising from six to twelve amino acids, or its functional equivalent, or a pharmaceutically acceptable salt thereof, said peptide having sequence SEQ ID NO:11 or a contiguous fragment thereof, in which up to three amino acid residues are replaced. Said peptide may comprise from six to eleven amino acids, and it is a contiguous fragment of sequence SEQ ID NO:11 in which up to three amino acid residues are replaced. Said fragment preferably comprises SEQ ID NO:1 (IKEKYP) in which up to one amino acid residue is replaced. Said peptide according to the invention is, in one embodiment, a hexapeptide comprising SEQ ID NO:1 (IKEKYP) in which up to one amino acid residue is replaced. A preferred peptide according to the invention comprises a hexapeptide comprising a sequence selected from the group consisting of IKEKYP (SEQ ID NO:1), IKAKYP (SEQ ID NO:2), IKEAYP (SEQ ID NO:3), and IAEKYP (SEQ ID NO:4). Further provided by the invention is a functional equivalent, or a pharmaceutically acceptable salt thereof, of a peptide having sequence SEQ ID NO:11 or the sequence of a contiguous fragment thereof, in which up to three amino acid residues are replaced, and which was derivatized by alkylation or esterification or cyclization.

The invention provides a pharmaceutical formulation containing a peptide comprising from six to eleven amino acids, or its functional equivalent, or a pharmaceutically acceptable salt thereof, said peptide having sequence SEQ ID NO:11 or a contiguous fragment thereof, in which up to three amino acid residues are replaced or its functional equivalent, or a pharmaceutically acceptable salt thereof. The invention further provides a pharmaceutical formulation containing a peptide, or its functional equivalent or a pharmaceutically acceptable salt thereof, comprising from six to twelve amino acids, being a contiguous fragment of sequence SEQ ID NO:11 in which up to three amino acid residues are replaced, for use in treating mood disorders.

DETAILED DESCRIPTION OF THE INVENTION

Low molecular compounds have now been provided, affecting the binding between calbindin and inositol monophosphatase (IMPase) and so reducing the activity of IMPase. It has been found that a fragment of IMPase, as small as hexapeptide, can interfere with the activating effect of calbindin on IMPase. Thus, lithium effects can be imitated and IMPase activity can be efficiently reduced, without incorporating lithium to the system or with a lower Li concentration, so reducing Li negative effects.

Calbindin D28k (calbindin), a member of the vitamin-D-dependent calcium-binding proteins, constitutes about 1% of total brain soluble protein. It binds to IMPase at amino acid residues 55-66, enhancing IMPase activity by several fold [Berggard et al., 2002]. In developing the present invention, said observation was employed for inhibiting IMPase activity at a different site than at lithium binding site. The inventors observed that addition of recombinant human calbindin increased IMPase activity of postmortem human prefrontal cortex crude homogenate by 3.5 fold [Shamir et al., 2005]. The in silico modeling of the interaction between IMPase and calbindin was carried out to identify the molecular requirements for optimal binding of the two proteins. For this purpose, the NMR structure of calbindin [Kojetin et al., 2006, Kordys et al., 2007] and the crystal structure of IMPase [Gill et al., 2005] were used. The modeled interaction indicated that the 55-66 segment of IMPase anchors calbindin via two lysine residues, Lys59 and Lys61 with a glutamate residue in between (a Lys-Glu-Lys motif). Integrated computational docking simulation was used by the inventors to predict peptide inhibitors, employing the model as a basis for designing short peptides predicted to inhibit the interaction between IMPase and calbindin. The effect of the rationally designed peptides on calbindin-activated IMPase activity in crude homogenates of mouse brain and postmortem human brain was measured in vitro. In one experiment, four different hexapeptides including at least part of the Lys-Glu-Lys motif inhibited calbindin-activated IMPase activity. These findings enable to inhibit IMPase activity at an alternative site than that of lithium.

A plausible model of the interaction between IMPase and calbindin was obtained using the docking program MolFit [Katchalski-Katzir et al., 1992] followed by energy minimization. Residues 55-66 of IMPase comprise the segment which has been shown to interact with calbindin [Berggard et al., 2002]. In the docking procedure residues 55-66 of IMPase were placed in the interface between the two proteins. In contrast, no restraints were imposed on the interacting surface of calbindin. In the modeled complex (not shown), optimal binding requirement were deduced. IMPase binds a groove formed by the N- and C-terminal domains of calbindin and interacts with the calcium binding loops.

The designed peptides were validated by in vitro IMPase activity measurements. As shown in the Examples (Table 1), IMPase activity of mouse brain crude homogenate is increased by 1.9 ±1.0 (S.D.) fold in the presence of 20 μM human recombinant calbindin. When 10 μM of Peptide 1 (SEQ ID NO:1) were added to the reaction mixture, the effect of calbindin on IMPase activity was strongly reduced. Peptides 2 through 4 (SEQ ID NO:2 through SEQ ID NO:4), which included the Lys-Glu-Lys motif or part of it, inhibited the activating interaction similarly to Peptide 1. Peptides 5 through 8 (SEQ ID NO:5 through SEQ ID NO:8), which included only one or none of the amino acids Lys or Glu, did not interfere with the enhancement of IMPase activity by calbindin. Peptides 9 and 10 (SEQ ID NO:9 and SEQ ID NO:10) of five and three residues, respectively, which contained an intact Lys-Glu-Lys motif did not interfere with the enhancement of IMPase activity by calbindin. The results suggest that Peptides 1 through 4 but not Peptides 5 through 10 contain the preferred residues that optimize the competition with IMPase on the interaction with calbindin. Table 1 shows that mouse brain IMPase activity in the presence of calbindin is significantly higher than that of the control, and that each of Peptides 1 through 4 inhibits this activation. The inhibitory effect of Peptide 1 on calbindin-activated IMPase was also demonstrated with postmortem human brain crude homogenate. Human recombinant calbindin increased human brain IMPase activity three-fold and Peptide 1 abolished this effect.

To control for a possible nonspecific effect of short peptides on IMPase activity the enzyme's activity in the presence of Peptide 1 (but in the absence of calbindin) was assessed. Peptide 1 did not affect the basal activity of IMPase. Furthermore, possibilities were checked that there was a protease activity in the homogenate, and that eventual prior interaction between IMPase and calbindin prevents interference by the active peptides. To this end calbindin was preincubated with the homogenate for 10 min prior to the addition of the substrate. No difference in IMPase activity was found in these two experiments.

Small molecule inhibitors have, thus, been provided here, competing with IMPase on the binding sites of calbindin. Once these peptides bind calbindin, activation of IMPase is hampered. The role of the Lys-Glu-Lys motif in the interaction between IMPase and calbindin has been experimentally assesses. In a preferred embodiment of the invention, a peptide is provided, or its derivative or salt, for inhibiting the binding of calbindin to inositol monophosphatase (IMPase), the peptide having from six to twelve amino acid residues and comprising a sequence derived from SEQ ID NO:1 by up to one amino acid replacement. Said peptide is preferably a hexapeptide comprising SEQ ID NO:11 or a sequence derived from it by one amino acid replacement. Said peptide may be selected from the group consisting of Peptide 1 to Peptide 4, having sequences from SEQ ID NO:1 to SEQ ID NO:4, respectively. In another aspect of the invention, the peptides having said sequences are derivatized, wherein said derivatization may comprise, for example, alkylation or esterification or cyclization. The derivatives included in the invention are pharmaceutically acceptable salts of said peptides.

Thus, the invention provides the means to affect the phosphoinositol signaling system, and mood disorders, by inhibiting a protein-protein interaction, wherein the inhibitor is a rationally designed small molecule. Said protein-protein interaction is calbindin-IMPase interaction, and said small molecule is a designed peptide having from six to twelve amino acid residues. The system may be employed for treating mood disorders and other conditions for which lithium is used. In one aspect, the invention aims at treating bipolar disorders by administering peptides described herein; in another aspect, the invention aims at treating bipolar disorder by combined administering peptides described herein with lithium.

Provided are novel mood stabilizers for treating bipolar disorders, and other disorders that benefit from lithium treatment. The peptides may be beneficial either as substitutes of lithium or as an add-on drug resulting in safer and more effective treatment.

This invention thus relates to a method of inhibiting the binding of calbindin to inositol monophosphatase (IMPase), comprising i) providing a peptide derivative or a pharmaceutically acceptable salt thereof, derived from SEQ ID NO:11 (ISSIKEKYPSHS), comprising from six to twelve amino acids; and ii) contacting either of said calbindin and said IMPase with said peptide derivative; wherein said peptide derivative is a contiguous fragment of SEQ ID NO:11 in which up to three amino acid residues are replaced, and which is optionally derivatized, wherein said derivatization may comprise, for example, alkylation or esterification or cyclization. In a preferred embodiment of the method of the invention, said fragment comprises SEQ ID NO:1 (IKEKYP) in which up to one amino acid residue is replaced. Said peptide derivative is advantageously a hexapeptide comprising SEQ ID NO:1 (IKEKYP) in which up to one amino acid residue is replaced; for example, selected from IKEKYP (SEQ ID NO:1), IKAKYP (SEQ ID NO:2), IKEAYP (SEQ ID NO:3), and IAEKYP (SEQ ID NO:4). Said method of inhibiting the binding between calbindin and IMPase is preferably utilized for reducing the positive stimulation of the IMPase activity by calbindin; said inhibiting results in decreasing activity of said IMPase, which can have positive effects on mood disorders. Said inhibiting preferably results in decreasing the activity of human IMPase in the presence of human calbindin D28k in vitro by at least 50%. The invention provides a hexapeptide, or a pharmaceutically acceptable salt thereof, comprising SEQ ID NO:1 (IKEKYP) in which up to one amino acid residue is replaced, and which is optionally derivatized, wherein said derivatization may comprise, for example, alkylation or esterification or cyclization. Provided by the invention is also a pharmaceutical formulation comprising said hexapeptide, and its use in treating mood disorders. The invention relates to a method of treating mood disorders, comprising i) providing a peptide derivative or a pharmaceutically acceptable salt thereof, derived from SEQ ID NO:11 (ISSIKEKYPSHS), comprising from six to twelve amino acids, wherein said peptide derivative is a contiguous fragment of SEQ ID NO:11 in which up to three amino acid residues are replaced, and which is optionally derivatized, wherein said derivatization may comprise, for example, alkylation or esterification or cyclization; and ii) administering said derivative or its salt to a subject in need of such treatment. In a preferred embodiment, provided is a method of treating mood disorders, comprising i) providing a hexapeptide, or a pharmaceutically acceptable salt thereof, comprising SEQ ID NO:1 (IKEKYP) in which up to one amino acid residue is replaced, and which is optionally derivatized, wherein said derivatization may comprise, for example, alkylation or esterification or cyclization; and ii) administering said derivative or its salt to a subject in need of such treatment.

The invention will be further described and illustrated by the following examples.

EXAMPLES

Example 1

Modeling the Structure of the Complex Between Impase and Calbindin

The crystal structure of IMPase (PDB entry 2bji) and the NMR structure of calbindin (PDB entry 2g9b) were used to model the structure of the complex using the protein-protein docking program MolFit [Katchalski-Katzir et al., 1992]. MolFit performs a comprehensive stepwise search of the rotation-translation space and evaluates each putative complex by the geometrical and chemical complementarity of the interacting surfaces [Berchanski et al., 2004]. In addition, MolFit allows up- or down-weighting of portions of the molecular surface based on experimental data and bioinformatics analyses [Ben-Zeev and Eisenstein, 2003]. Weighted-geometric, geometric-electrostatic and geometric-hydrophobic rotation-translation scans were executed producing three lists of docking models; the lists were intersected such that the final list included only models that appeared in all three lists [Berchanski et al., 2004]. The weighted-geometric docking emphasized interactions involving residues 55-66 of IMPase. In addition, the final list was screened to include only models in which residues 55-66 of IMPase were in contact with calbindin. Only a small number of models were retained and the top ranking docking models were energy minimized. Four $Ca^{+2}$ ions were modeled into the EF sub-domains of calbindin (EF1, EF3, EF4 and EF5). The backbone atoms of IMPase were restrained to their starting positions during the minimization except for the calbindin binding loop 55-66. Distance restraints were imposed on a large number of randomly selected pairs of Cα atoms within each of the three domains of calbindin (EF1-EF2, EF3-EF4 and EF5-EF6) excluding loop regions. In this way the overall fold of each domain was not disrupted but relative movement of the domains was allowed as well as movement of the calbindin molecule as a whole with respect to IMPase. The complex was immersed in a layer of 7Å of water molecules and several intermittent energy minimization and molecular dynamics cycles were performed in order to reach an energy minimum.

Example 2

Peptides Design Based on the Modeled Complex

The resulting model was used as a basis for designing ten short peptides (Table 1). Peptide 1, a hexapeptide (Seq ID NO:1), was composed of an identical sequence as residues 58-63 of IMPase (Ile-Lys-Glu-Lys-Tyr-Pro). These six amino acids are the central sequence of the previously reported 12 amino acid segment (residues 55-66, SEQ ID NO:11) of IMPase shown to interact with calbindin [Berggard et al., 2002]. Furthermore, this specific 6-mer peptide is fully conserved between mouse and human.

These six amino acids include Lys59 and Lys61, separated by Glu60 designated the Lys-Glu-Lys motif. Additional three 6-mer peptides included at least part of the Lys-Glu-Lys motif (Peptides 2-4, SEQ ID NOs: 2-4). In Peptide 2 we kept the Lys-Glu-Lys motif and permutated Glu60 to alanine. Peptides 3 and 4 are similar to Peptide 1 but in each peptide one of the Lys residues was permutated to alanine. Four other 6-mer peptides included only one or none of the amino acids Lys or Glu (Peptides 5-8, SEQ ID NOs: 5-8). In Peptide 5 one of the lysine residues and Ile58 were permutated to histidine and serine, respectively, and the whole sequence has been scrambled. Peptide 6 was composed of the same sequence as Peptide 1 but the two lysine residues were permutated into alanine.

fied spectrophotometrically in an ELISA reader (iEMS, Labsystems) using the malachite green color reagent. To study the effect of the synthetic peptides on the enhancing interaction between calbindin and IMPase the reaction was carried out in the presence of 20 µM human recombinant calbindin [Thulin and Linse, 1999] (produced by PPS, Rehovot, Israel, using the plasmid kindly donated by S. Linse, Lund, Sweden) and in the presence or absence of 10 µM of each of the peptides. In order to distinguish IMPase activity from non-specific phosphatases the reaction was carried out in the presence and absence of 30 mM LiCl. LiCl is a specific inhibitor of this enzyme [Hallcher and Sherman, 1980] and at this concentration totally inhibits IMPase activity. The enzyme activity was calculated as the difference between the activity values in

TABLE 1

Mouse brain crude homogenate IMPase activity in the presence of recombinant human calbindin and specific short peptides (SEQ ID NO: 1 to SEQ ID NO: 10)

| Treatment | Peptide Sequence | n | IMPase Activity, mean ± SD | % Inhibition of Calbindin Activation | p* |
|---|---|---|---|---|---|
| control | — | 35 | 1.0 ± 0.5 | — | |
| | | | | | <0.000 |
| + calbindin | — | 33 | 1.9 ± 1.0 | — | 1** |
| + calbindin + Peptide 1 | Ile-Lys-Glu-Lys-Tyr-Pro | 34 | 1.2 ± 0.9 | 78 | <0.002 |
| + calbindin + Peptide 2 | Ile-Lys-Ala-Lys-Tyr-Pro | 12 | 0.9 ± 0.5 | 100 | <0.003 |
| + calbindin + Peptide 3 | Ile-Lys-Glu-Ala-Tyr-Pro | 9 | 1.0 ± 0.5 | 100 | <0.02 |
| + calbindin + Peptide 4 | Ile-Ala-Glu-Lys-Tyr-Pro | 12 | 1.1 ± 0.6 | 89 | <0.02 |
| + calbindin + Peptide 5 | Ser-Tyr-Glu-His-Lys-Pro | 9 | 1.4 ± 0.6 | 56 | NS |
| + calbindin + Peptide 6 | Ile-Ala-Glu-Ala-Tyr-Pro | 4 | 2.5 ± 1.1 | 0 | NS |
| + calbindin + Peptide 7 | Lys-His-Ile-Lys-Pro-Ser | 3 | 1.4 ± 0.2 | 56 | NS |
| + calbindin + Peptide 8 | Ile-Ala-Ala-Ala-Tyr-Pro | 4 | 2.3 ± 1.7 | 0 | NS |
| + calbindin + Peptide 9 | Ile-Lys-Glu-Lys-Tyr | 5 | 1.9 ± 0.6 | 0 | NS |
| + calbindin + Peptide10 | Lys-Glu-Lys | 4 | 2.6 ± 1.2 | 0 | NS |

*Student's t-test
**vs. control

Peptide 7 contained random permutations but still included two lysine residues albeit, separated by two, rather than a single residue, none of which was glutamate. Peptide 8 was also composed of the same sequence as Peptide 1 but the whole Lys-Glu-Lys motif has been permutated to three alanine residues. One 5-mer peptide included the Lys-Glu-Lys motif but lacked the carboxyterminal Pro (Peptide 9, SEQ ID NO:9). One 3-mer peptide was composed of the Lys-Glu-Lys motif only (Peptide 10, SEQ ID NO:10). The peptides were custom-synthesized by GeneScript Corporation, Scotch Plains, N.J.

Example 3

IMPase Activity

IMPase activity in mouse brain homogenates was measured as previously described [Cryns et al., 2008]. Inorganic phosphate liberated from inositol-1-phosphate was quantified absence and in the presence of Li. Values were normalized to the mean of the control values in each run.

Example 4

Peptide Administration

In preliminary experiments, the in-vitro effective peptides are administered to mice, either intra-cerebro-ventricularly via an indwelled canule or using a blood brain barrier vehicle. The mice will be studied in behavioral animal models attenuated by Li treatment, comprising pilocarpine-induced seizures paradigm of lithium action, amphetamine-induced hyperactivity model of mania, and Porsolt forced-swim test model of depression. Protocols of experiments are approved by the Ben-Gurion University animal experimentation ethics committee and are in line with the NIH guide for the use of laboratory animals.

While the invention has been described using some specific examples, many modifications and variations are possible. It is therefore understood that the invention is not intended to be limited in any way, other than by the scope of the appended claims.

REFERENCES

Atack, J. R. (1997) Inositol monophosphatase inhibitors--lithium mimetics? *Med Res Rev*, 17, 215-24.

Ben-Zeev, E. & Eisenstein, M. (2003) Weighted geometric docking: incorporating external information in the rotation-translation scan. *Proteins*, 52, 24-7.

Berchanski, A., Shapira, B. & Eisenstein, M. (2004) Hydrophobic complementarity in protein-protein docking. *Proteins*, 56, 130-42.

Berggard, T., Szczepankiewicz, O., Thulin, E. & Linse, S. (2002) Myo-inositol monophosphatase is an activated target of calbindin D28k. *J Biol Chem*, 277, 41954-9.

Cryns, K., Shamir, A., Van Acker, N., Levi, I., Daneels, G., Goris, I., Bouwknecht, J. A., Andries, L., Kass, S., Agam, G., Belmaker, H., Bersudsky, Y., Steckler, T. & Moechars, D. (2008) IMPA1 is essential for embryonic development and lithium-like pilocarpine sensitivity. *Neuropsychopharmacology*, 33, 674-84.

Fauroux, C. M. & Freeman, S. (1999) Inhibitors of inositol monophosphatase. *J Enzyme Inhib*, 14, 97-108.

Gill, R., Mohammed, F., Badyal, R., Coates, L., Erskine, P., Thompson, D., Cooper, J., Gore, M. & Wood, S. (2005) High-resolution structure of myo-inositol monophosphatase, the putative target of lithium therapy. *Acta Crystallogr D Biol Crystallogr*, 61, 545-55.

Hallcher, L. M. & Sherman, W. R. (1980) The effects of lithium ion and other agents on the activity of myo- inositol-1-phosphatase from bovine brain. *J Biol Chem*, 255, 10896-901.

Harwood, A. J. & Agam, G. (2003) Search for a common mechanism of mood stabilizers. *Biochem Pharmacol*, 66, 179-89.

Katchalski-Katzir, E., Shariv, I., Eisenstein, M., Friesem, A. A., Aflalo, C. & Vakser, I. A. (1992) Molecular surface recognition: determination of geometric fit between proteins and their ligands by correlation techniques. *Proc Natl Acad Sci U S A*, 89, 2195-9.

Kojetin, D. J., Venters, R. A., Kordys, D. R., Thompson, R. J., Kumar, R. & Cavanagh, J. (2006) Structure, binding interface and hydrophobic transitions of Ca2+-loaded calbindin-D(28K). *Nat Struct Mol Biol*, 13, 641-7.

Kordys, D. R., Bobay, B. G., Thompson, R. J., Venters, R. A. & Cavanagh, J. (2007) Peptide binding proclivities of calcium loaded calbindin-D28k. *FEBS Lett*, 581, 4778-82.

Ohnishi, T., Ohba, H., Seo, K. C., Im, J., Sato, Y., Iwayama, Y., Furuichi, T., Chung, S. K. & Yoshikawa, T. (2007) Spatial expression patterns and biochemical properties distinguish a second myo-inositol monophosphatase IMPA2 from IMPA1. *J Biol Chem*, 282, 637-46.

Shamir, A., Elhadad, N., Belmaker, R. H. & Agam, G. (2005) Interaction of calbindin D and inositol monophosphatase in human postmortem cortex: possible implications for bipolar disorder. *Bipolar Disord*, 7, 42-8.

Thulin, E. & Linse, S. (1999) Expression and purification of human calbindin D28k. *Protein Expr Purif*, 15, 265-70.

The invention claimed is:

1. A method of reducing inositol monophosphatase (IMPase) activity in vivo, comprising
   i) providing a hexapeptide IKEKYP (SEQ ID NO:1) in which up to one amino acid residue is replaced, a functional equivalent of the hexapeptide obtained by alkylation, esterification, or cyclization, or a pharmaceutically acceptable salt thereof; and
   ii) contacting human IMPase in vivo in the presence of human calbindin D28k with said hexapeptide, thereby reducing the activating effect of said calbindin on said IMPase,
   wherein said hexapeptide interferes with binding of human calbindin D28k to human IMPase in vitro and reduces the activity of IMPase by at least 50% in vitro.

2. The method according to claim 1, wherein said contacting comprises administering said hexapeptide to a human subject in need of reducing IMPase activity by using a blood brain barrier vehicle.

3. The method according to claim 2, further comprising administering lithium.

4. The method of claim 2, wherein said subject is in need of treating mood disorders or other CNS disorders that benefit from lithium treatment.

* * * * *